(12) United States Patent
DeMarco

(10) Patent No.: US 7,364,655 B2
(45) Date of Patent: Apr. 29, 2008

(54) METHOD AND APPARATUS FOR INJECTING A SAMPLE INTO A CHROMATOGRAPHY SYSTEM

(75) Inventor: Nicholas DeMarco, Burlington, WI (US)

(73) Assignee: Varian, Inc., Palo Alto, CA (US)

( * ) Notice: Subject to any disclaimer, the term of this patent is extended or adjusted under 35 U.S.C. 154(b) by 506 days.

(21) Appl. No.: 11/086,861

(22) Filed: Mar. 22, 2005

(65) Prior Publication Data
US 2006/0213822 A1  Sep. 28, 2006

(51) Int. Cl.
*B01D 15/08* (2006.01)
(52) U.S. Cl. .................... 210/198.2; 210/656
(58) Field of Classification Search ............. 210/635, 210/656, 657, 659, 198.2, 232, 238; 141/12, 141/73, 80; 95/82; 96/101
See application file for complete search history.

(56) References Cited

U.S. PATENT DOCUMENTS 3,487,938 A * 1/1970 Patterson ................. 210/198.2
4,758,340 A * 7/1988 Marchand et al. ........ 210/198.2
4,865,728 A * 9/1989 Larsson .................... 210/198.2
5,188,730 A * 2/1993 Kronwald ................. 210/198.2
5,366,621 A * 11/1994 Bidell et al. .............. 210/198.2
5,378,361 A * 1/1995 Baeckstrum .............. 210/198.2
5,951,873 A * 9/1999 Shalon et al. ............... 210/656

OTHER PUBLICATIONS

BIOTAGE, Inc.; "Sample Injection Modules Simplify Loading (SIM)™;" http://www.biotage.com/pharmrnd/tech_sample.cfm; printed on Feb. 2, 2002, 2 pages.

* cited by examiner

*Primary Examiner*—Ernest G. Therkorn

(57) ABSTRACT

A method and apparatus for injecting a sample into a chromatography system. The apparatus can include a tubular housing having an inner surface and an open end, and a cap coupled to the open end of the tubular housing. The cap can include an aperture therethrough. The apparatus can further include a rod positioned through the aperture in the cap and including a piston at one end. The piston can include an outer edge in contact with the inner surface of the tubular housing. The apparatus can further include a lever coupled to the cap, wherein the lever engages the rod and substantially prevents movement of the rod in a first direction while allowing movement in a second direction substantially opposite the first direction.

13 Claims, 3 Drawing Sheets

METHOD AND APPARATUS FOR INJECTING A SAMPLE INTO A CHROMATOGRAPHY SYSTEM

BACKGROUND

The present invention relates to methods and apparatuses for injecting a sample to be analyzed into a chromatography system, and particularly, into a liquid chromatography system. Typically, sample injection apparatuses for liquid chromatography systems include syringes having a barrel and a plunger. The sample can be dissolved in a solvent and adsorbed a stationary phase to form a stationary phase coated with the sample of interest. The coated stationary phase can be loaded into the barrel of the syringe, or the barrel can be pre-filled with the uncoated stationary phase, and the sample of interest can be run through the stationary phase in the barrel of the syringe to coat the stationary phase with the sample of interest.

The coated stationary phase is held in place in the barrel of the syringe between two frits. The plunger can be used to contact an upper frit. The sample injection apparatus can be connected to a fluid line of the liquid chromatography system, and chromatography solvent can be delivered through the plunger, through the upper frit, and into the coated stationary phase. The sample can then be eluted from the coated stationary phase out an outlet of the syringe into the liquid chromatography system. Due to the build-up of back pressure in the syringe, the plunger can back out of the syringe, causing inadequate or undesirable sample injection. Some devices have attempted to lock the plunger in place to prevent the plunger from backing out of the syringe.

Such locking devices have included a series of depressions or apertures along the plunger. A fastener, such as a screw, can be positioned in engagement with a depression or aperture in the plunger to lock the position of the plunger relative to the barrel. In this way, such conventional systems can be cumbersome. Other similar locking devices can include teeth or protrusions that engage depressions or apertures in the plunger, but similar problems arise.

SUMMARY

The present invention provides an apparatus for injecting a sample into a chromatography system. In some embodiments, the apparatus includes a tubular housing having an inner surface and an open end, and a cap coupled to the open end of the tubular housing. The cap includes an aperture therethrough. The apparatus furthers include a rod positioned through the aperture in the cap and having a piston coupled at one end. The piston has an outer edge in contact with the inner surface of the tubular housing. The apparatus further includes a lever coupled to the cap, wherein the lever engages the rod and substantially prevents movement of the rod in a first direction while allowing movement in a second direction substantially opposite the first direction.

The present invention provides an apparatus for injecting a sample into a chromatography system is provided. In some embodiments, the apparatus includes a tubular housing having a longitudinal axis, an open end, an inner surface and an outwardly-protruding flange adjacent the open end. The apparatus furthers includes a cap dimensioned to cover the open end of the tubular housing. The cap includes a plug portion dimensioned to be received within the open end of the tubular housing, and a gripping portion coupled to at least a portion of the flange of the tubular housing. The apparatus further includes a rod having a longitudinal axis generally parallel with the longitudinal axis of the tubular housing. The rod includes a first end and a second end. The apparatus further includes a piston coupled to the first end of the rod. The piston protrudes outwardly from the rod to define an outer surface. The outer surface of the piston is dimensioned to engage the inner surface of the tubular housing when positioned within the tubular housing. The apparatus further includes a lever pivotally coupled to the cap and movable between a first position in which the lever engages the rod to substantially prevent movement of the rod in a first direction while allowing movement in a second direction substantially opposite the first direction and a second position in which the lever allows movement of the rod in the first direction and the second direction. The apparatus further includes a biasing element positioned to bias the lever in the first position.

The present invention provides an apparatus for injecting a sample into a chromatography system. In some embodiments, the apparatus includes a tubular housing having a longitudinal axis, an open end, an inner surface and an outwardly-protruding flange adjacent the open end. The apparatus further includes a cap dimensioned to cover the open end of the tubular housing. The cap includes a plug portion dimensioned to be received within the open end of the tubular housing and having an aperture therethrough, and a gripping portion coupled to at least a portion of the flange of the tubular housing. The apparatus further includes a rod having a longitudinal axis generally parallel with the longitudinal axis of the tubular housing. The rod is positioned through the aperture in the plug portion of the cap and includes a first end and a second end. The apparatus further includes a piston coupled to the first end of the rod. The piston protrudes outwardly from the rod to define an outer surface. The outer surface of the piston is dimensioned to engage the inner surface of the tubular housing when positioned within the tubular housing. The apparatus further includes a lever having an aperture through which the rod is positioned. The lever is pivotally coupled to the cap and movable between a first position in which the lever engages the rod to substantially prevent movement of the rod in a first direction while allowing movement in a second direction substantially opposite the first direction and a second position in which the lever allows movement of the rod in the first direction and the second direction. The lever is positioned at an acute angle with respect to the longitudinal axis of the rod when in the first position, and the lever is positioned at a substantially right angle with respect to the longitudinal axis of the rod when in the second position. The apparatus further includes a biasing element positioned to bias the lever in the first position.

Other features and aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Furthermore, terms such as "front," "rear," "top," "bottom," "upwardly," "downwardly," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Figure 1:
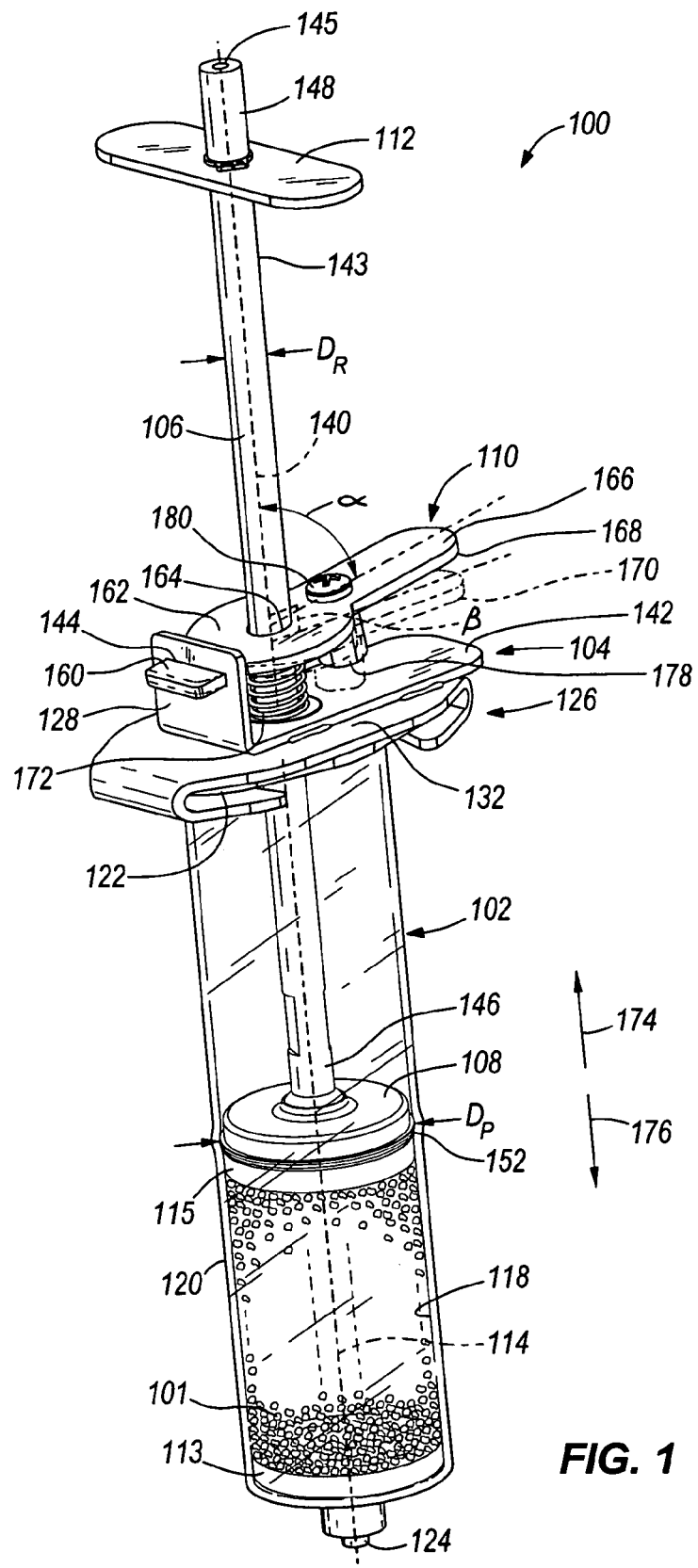
FIG. 1 is a perspective view of a sample injection apparatus according to one embodiment of the present invention.
Figure 2:
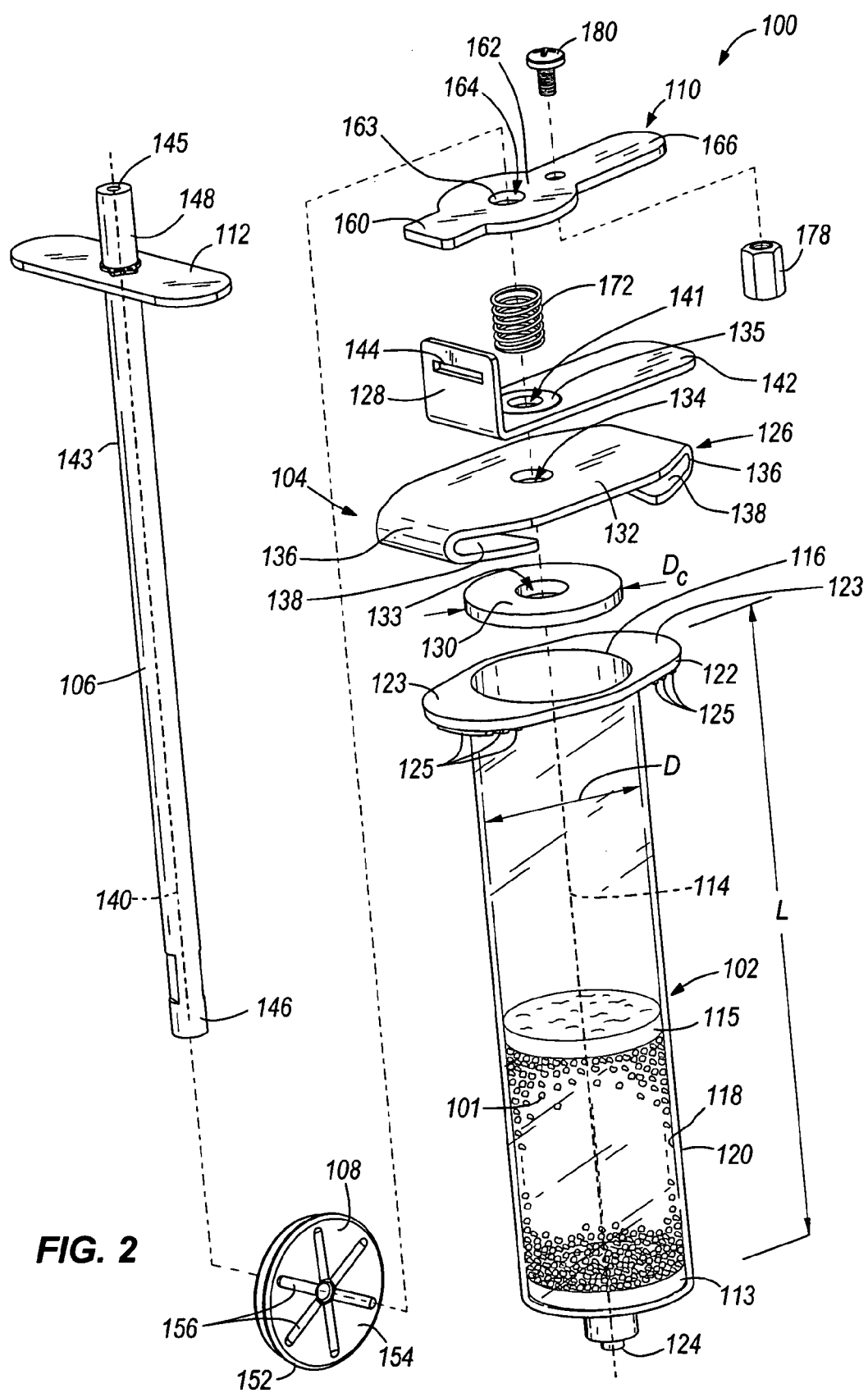
FIG. 2 is an exploded view of the sample injection apparatus of FIG. 1.

FIGS. 1 and 2 illustrate a sample injection apparatus 100 according to one embodiment of the present invention. The sample injection apparatus 100 includes a tubular housing 102 containing a first stationary phase 101, a cap 104, a rod 106, a piston 108, a lever 110, and a handle 112. As shown in FIGS. 1 and 2, the first stationary phase 101 is bounded on a first end by a first frit 113, or other porous member, and on a second end by a second frit 115. The first stationary phase 101 can be in fibrous or particulate form, and can include at least one of a silica-based stationary phase (e.g., silica particles with various hydrocarbon coatings, including, without limitation, a two-carbon alkane coating (C2), an eight-carbon alkane coating (C8), a ten-carbon alkane coating (C10), an eighteen-carbon alkane coating (C18), a phenol coating (PH), a diol coating (OH), and the like); an alumina-based stationary phase; a FLOROSIL™-brand magnesium silicate stationary phase (available from U.S. Silica Company); and a polystyrene divinylbenzene-based stationary phase (PS-DVB).

The sample injection apparatus 100 allows a sample of interest to be dissolved, adsorbed to the first stationary phase 101, and injected into a chromatography system to be analyzed and/or separated into its constituents, or fractions. For example, the sample of interest can be dissolved in a first solvent (which can be formed of one or more solvents), loaded into the tubular housing 102, adsorbed to the first stationary phase 101 by removing the first solvent (e.g., by heat, vacuum, gravity, and/or time), and injected with a second solvent (which can be formed of one or more solvents) into a chromatography cartridge containing a second stationary phase. The second stationary phase can be adapted to interact with the sample of interest to separate the sample into its fractions. In some embodiments, the first and second stationary phases are the same, and in some embodiments, the first and second stationary phases are different. In some embodiments, the first and second solvents are the same, and in some embodiments, the first and second solvents are different. The first and second solvents can each include at least one of hexanes, heptane, iso-octane, diethyl ether, ethyl acetate, methanol, ethanol, propanol, dichloromethane, acetonitrile, chloroform, toluene, acetone, tetrahydrofuran, and combinations thereof.

In the embodiment shown in FIGS. 1 and 2, the tubular housing 102 is pre-filled with the first stationary phase 101, and packed between the first and second frits 113 and 115. In other embodiments, the first stationary phase 101 and the first and second frits 113 and 115 can be added to the tubular housing 102 by a user after at least partially coating the stationary phase 101 with the sample of interest.

The tubular housing 102 is generally cylindrical in shape and has a length L and an inner diameter D. The inner diameter D is generally uniform along the length L of the tubular housing 102. The tubular housing 102 includes a longitudinal axis 114, an open end 116, an inner surface 118, and an outer surface 120. The tubular housing 102 can further include a flange 122 that extends outwardly from the outer surface 120 adjacent the open end 116. The flange 122 includes two wing-shaped portions 123 that are positioned on opposite sides of the open end 116 from one another. However, other shapes of flanges 122 are possible and within the spirit and scope of the present invention, including, without limitation, a circular flange, a square flange, a triangular flange, and the like.

The tubular housing 102 can further include an outlet port 124 that can be shaped and dimensioned to be coupled to a chromatography system (e.g., a chromatography cartridge in a chromatography system) to provide fluid communication between the tubular housing 102 and a fluid line in the chromatography system.

The tubular housing 102 can be formed of a variety of materials including, without limitation, at least one of polyethylene, polypropylene, polyethylene terephthalate (PET), polyamide, polyvinyl chloride, polytetrafluoroethylene (e.g., TEFLON®-brand polytetrafluoroethylene (PTFE), DuPont Corporation), a polymer of tetrafluoroethylene and hexafluoropropylene (FEP; e.g., Dyneon™-brand FEP fluorothermoplastic, 3M Corporation), a fiberglass and PTFE composite (e.g., TEFLEX®-brand fiberglass sheets coated with TEFLON®-brand PTFE, DuPont Corporation), other chemically-inert materials, and the like.

The cap 104 is positioned to cover the open end 116 of the tubular housing 102. The cap 104 is formed of a metal, and particularly in the illustrated embodiment, stainless steel sheet metal. The cap 104 includes a main portion 126 and a tab 128 extending from the main portion 126. The main portion 126 includes a plug portion 130 dimensioned to be received in the open end 116 of the tubular housing 102, and a gripping portion 132 that can be coupled to the flange 122 of the tubular housing 102.

The plug portion 130 can be cylindrical in shape to match the shape of the tubular housing 102 and can have an outer diameter $D_c$ no greater than about the inner diameter D of the tubular housing 102. The gripping portion 132 of the main portion 126 of the cap 104 can include two wing-shaped portions 136, and each of the wing-shaped portions 136 can include a recess 138 that is shaped and dimensioned to receive a wing-shaped portion 123 of the flange 122 of the tubular housing 102. The wing-shaped portions 123 of the flange 122 can each include one or more ribs or protrusions 125 on an upper or lower surface to enhance a press-fit engagement between the wing-shaped portions 123 of the flange 122 and the wing-shaped portions 136 of the gripping portion 132 of the cap 104.

The plug portion 130 includes an aperture 133 dimensioned to allow the rod 106 to pass therethrough. The gripping portion 132 includes an aperture 134 that coincides with the aperture 133 of the plug portion 130 and that is also dimensioned to allow the rod 106 to pass therethrough. The apertures 133 and 134 together define an aperture in the cap 104. As shown in FIG. 2, one or more O-rings 135 can be positioned about the rod 106 adjacent the plug portion 130 and the gripping portion 132 to fluidly seal the apertures 133 and 134. The plug portion 130 and the gripping portion 132 can be coupled in a variety of suitable manners, including, without limitation, with at least one of a fastener (e.g., a screw, a nail, a rivet, a bolt, and the like), welding, brazing, soldering, adhesives, magnets, and the like. In some embodiments, the plug portion 130 and the gripping portion 132 are coupled together by being integrally formed.

The tab 128 of the cap 104 is shown in the embodiment illustrated in FIGS. 1 and 2 as extending upwardly from the main portion 126 of the cap 104, substantially parallel to a longitudinal axis 140 of the rod 106. However, the tab 128 can extend outwardly from the main portion 126 of the cap 104 in a variety of other manners, and need not be oriented parallel to the longitudinal axis 140 of the rod 106. The tab 128 includes a slot 144 having a generally rectangular shape, but a variety of slot shapes can be used without departing from the spirit and scope of the present invention. The slot 144 allows at least a portion of the lever 110 to be hinged to the tab 128 by passing through the slot 144. The lever 110 will be described in greater detail below.

In the illustrated embodiment, the cap 104 includes an L-shaped bracket 142 that is coupled to the main portion 126 of the cap 104 by welding, and the L-shaped bracket 142 defines the tab 128. The L-shaped bracket 142 includes an aperture 141 dimensioned to allow the rod 106 to pass therethrough. In embodiments employing the L-shaped bracket 142, the apertures 133, 134 and 141 together define an aperture in the cap 104. The L-shaped bracket 142 can be coupled to the rod 106 in a variety of suitable manners, including, without limitation, using at least one of a fastener (e.g., a rivet, a screw, a nail, a bolt, and the like), a magnet, adhesive, soldering, brazing, and the like. Alternatively, the L-shaped bracket 142 can be coupled to the main portion 126 of the cap 104 by being integrally formed with the main portion 126. The tab 128 need not be defined by the L-shaped bracket 142. That is, the sample injection apparatus 100 need not include the L-shaped bracket 142. The tab 128 can itself be coupled to the main portion 126 by any of the manners described above.

The rod 106 is generally annular in shape, and includes an outer surface 143, an outer diameter $D_R$, and a bore 145 to allow fluid to pass therethrough. The rod 106 passes through the apertures 133 and 134 in the cap 104, and includes a first end 146 and a second end 148. The piston 108 is coupled to the first end 146 of the rod 106 to be positioned within the tubular housing 102. In some embodiments, the second end 148 of the rod 106 can be coupled to other equipment (e.g., an automated drive device) that can press the rod 106 downwardly to drive the piston 108 downwardly in the tubular housing 102, or that can pull the rod 106 upwardly to back the piston 108 out of the tubular housing 102. The handle 112 is coupled to the rod 106 adjacent the second end 148 of the rod, and the handle 112 can be used to move the rod 106 upwardly or downwardly relative to the tubular housing 102. The handle 112 can be grasped by a user, or other equipment can be coupled to the rod 106 via the handle 112. The illustrated handle 112 is coupled to the rod 106 between two ring-shaped clamps that are each dimensioned to be received in a circumferential groove on the rod 106. However, the handle 112 can be coupled to the rod 106 in a variety of suitable manners, such as those described above.

Alternatively, the handle 112 can be coupled to the rod 106 by being integrally formed with the rod 106. The handle 112 is shown by way of example only, but one of ordinary skill in the art would understand that a variety of other handles can be used to accomplish the same function without departing from the spirit and scope of the present invention.

The bore 145 can be fluidly coupled to a fluid line of a chromatography system to allow one or more solvents to be passed into the tubular housing 102 via the rod 106. As a result, the bore 145 of the rod 106 and the outlet port 124 of the tubular housing 102 allow the sample injection apparatus 100 to be in fluid communication with at least a portion of a fluid line of a chromatography system.

In the embodiment illustrated in FIGS. 1 and 2, the piston 108 is formed of metal and is coupled to the rod 106 via welding. The piston 108 can be formed of a variety of rigid or semi-rigid materials, including, without limitation, at least one of stainless steel, polytetrafluoroethylene (PTFE, e.g., TEFLON®-brand PTFE), polypropylene, aluminum, a composite material comprising PTFE (e.g., TEFLON®-brand PTFE) and fibers or particles formed of at least one of carbon or glass, polyetheretherketone (PEEK™, available from Victrex®), and the like. Depending at least partially on the material make-up of the piston 108, the piston 108 can be coupled to the rod 106 in a variety of suitable manners, including, without limitation, using at least one of a fastener (e.g., a rivet, a screw, a nail, a bolt, and the like), a magnet, adhesive, soldering, brazing, and the like. In some embodiments, the piston 108 can be coupled to the rod 106 by being integrally formed with the rod 106, e.g., by casting, machining, molding, and the like. The piston 108 can be formed of a variety of other rigid materials, as will be described in greater detail below with reference to FIG. 3.

The piston 108 is generally cylindrical in shape, and includes an outer surface or edge 152 that contacts or engages the inner surface 118 of the tubular housing 102 when positioned within the tubular housing 102. The piston 108 includes an outer diameter $D_P$ that is greater than or equal to the inner diameter D of the tubular housing 102. For example, in some embodiments, as shown in FIGS. 1 and 2, the outer diameter $D_P$ is slightly greater than the inner diameter D of the tubular housing 102. Because the piston 108 is formed of a more rigid material than the tubular housing 102, the piston 108 (and particularly, the outer surface 152) locally, elastically, deforms the tubular housing 102 as the piston 108 is moved up and down within the tubular housing 102, as shown in FIG. 1. As a result, the inner diameter D of the tubular housing 102 is temporarily increased at a point along the length L of the tubular housing 102 coinciding with the position of the piston 108. This deformation creates a fluid seal between the outer surface 152 of the piston 108 and the inner surface 118 of the tubular housing 102.

In the embodiment illustrated in FIGS. 1 and 2, the outer edge 152 of the metal piston 108 is highly polished to achieve a smooth finish that allows the piston 108 to easily slide up and down along the inner surface 118 of the tubular housing 102 substantially without marring or otherwise damaging the inner surface 118 of tubular housing 102. The polished surface also assists in creating an adequate seal between the outer surface 152 of the piston 108 and the inner surface 118 of the tubular housing 102.

In some embodiments, as shown in FIGS. 1 and 2, the piston 108 includes a bottom face 154 that includes a series of radially-extending grooves 156. The radially-extending grooves 156 facilitate the distribution of solvent (e.g., including the sample of interest) radially outward from the bore 145 of the rod 106, or the center of the tubular housing 102, toward the inner surface 118 of the tubular housing 102. The grooves 156 can provide improved mixing and distribution of the solvent and/or sample of interest within the tubular housing 102 prior to injection into the chromatography system. The grooves 156 can be deep enough to improve distribution of the solvent and/or sample, but shallow enough (i.e., not so voluminous) that the chromatographic analysis to be performed on the sample of interest is delayed or otherwise adversely affected.

As shown in FIG. 1, the lever 110 includes a first portion 160 dimensioned to be received in the slot 144 of the tab 128 of the cap 104. The lever 110 further includes a second portion 162 having an inner surface 163 that defines an aperture 164 through which the rod 106 passes, and a third portion 166 that can be manipulated to move the lever 110 from a first position 168 to a second position 170 (shown in dashed lines in FIG. 1). As shown in FIGS. 1 and 2, the aperture 164 in the second portion 162 of the lever 110 is slightly larger than the outer diameter $D_R$ of the rod 106. Particularly, the aperture 164 shown in FIGS. 1 and 2 is generally circular and has a diameter that is slightly greater than the outer diameter $D_R$ of the rod 106. As a result, the lever 110 can be pivoted about the slot 144 in the tab 128 to increase, decrease, or completely eliminate the amount of contact between the inner surface 163 that defines the aperture 164 and the outer surface 143 of the rod 106. The lever 110 is biased in the first position 168 by a biasing element (e.g., a coil spring 172, a leaf spring, an elastic bumper, and the like). In the first position 168, the lever 110 is positioned at an acute angle α with respect to the longitudinal axis 140 of the rod 106, which causes the inner surface 163 of the lever 110 to contact the outer surface 143 of the rod 106 to create a uni-directional lock on the rod 106 as a result of the inner surface 163 wedging against the outer surface 143 of the rod 106. Particularly, when the lever 110 is biased in the first position 168 by the spring 172, the lever 110 substantially prevents movement of the rod 106 in a first direction 174 substantially parallel with the longitudinal axis 114 of the tubular housing 102, while allowing movement of the rod 106 in a second direction 176 substantially opposite the first direction 174.

When the third portion 166 of the lever 110 is pressed downwardly, against the bias of the spring 172, the lock on the rod 106 is released. A downwardly-protruding boss 178 is coupled to the third portion 166 of the lever 110. The boss 178 contacts the cap 104 as the lever 110 is pressed downwardly. As a result, the boss 178 defines the second position 170 of the lever 110, as shown in FIG. 1. In the second position 170, the lever 110 is positioned at a substantially right angle β with respect to the longitudinal axis 140 of the rod 106. Because the aperture 164 in the lever 110 is slightly larger than the outer diameter $D_R$ of the rod 106, when the lever 110 is in the second position 170, the rod 106 is allowed to move in both the first direction 174 and the second direction 176. In FIGS. 1 and 2, the boss 178 is shown as being coupled to the lever 110 by a screw 180. However, the boss 178 can be coupled to the lever 110 in a variety of suitable manners, including, without limitation, using at least one of a fastener (e.g., nail, a bolt, a rivet, and the like), a magnet, adhesive, welding, soldering, and the like. In some embodiments, the boss 178 is coupled to the lever 110 by being integrally formed with the lever 110.

The following method can be used to prepare the sample of interest for injection into a chromatography system, using the sample injection apparatus 100. First, the sample of interest is dissolved in a first solvent in a container separate from the tubular housing 102, and the dissolved sample is then loaded into the pre-filled tubular housing 102 having the first stationary phase 101 packed between the first frit 113 and the second frit 115. The sample can be loaded into the tubular housing 102 using a variety of techniques known to those of ordinary skill in the art, including, without limitation, at least one of decanting, pipetting, and the like. The sample of interest is then allowed to pass through the first stationary phase 101 to adsorb to the first stationary phase 101, and at least partially form a coating on the first stationary phase 101. Vacuum can be applied to the tubular housing 102 to assist in distribution of the sample throughout the first stationary phase 101. In embodiments employing a different first and second solvent, the first solvent can be removed. The first solvent can be removed using at least one of heat, vacuum pressure, gravity, time, and combinations thereof. After the first solvent has been removed, the tubular housing 102 includes the first stationary phase 101 with the sample of interest adsorbed to it and distributed throughout it. The sample can then be injected into a chromatography system using the method described below.

Figure 3:
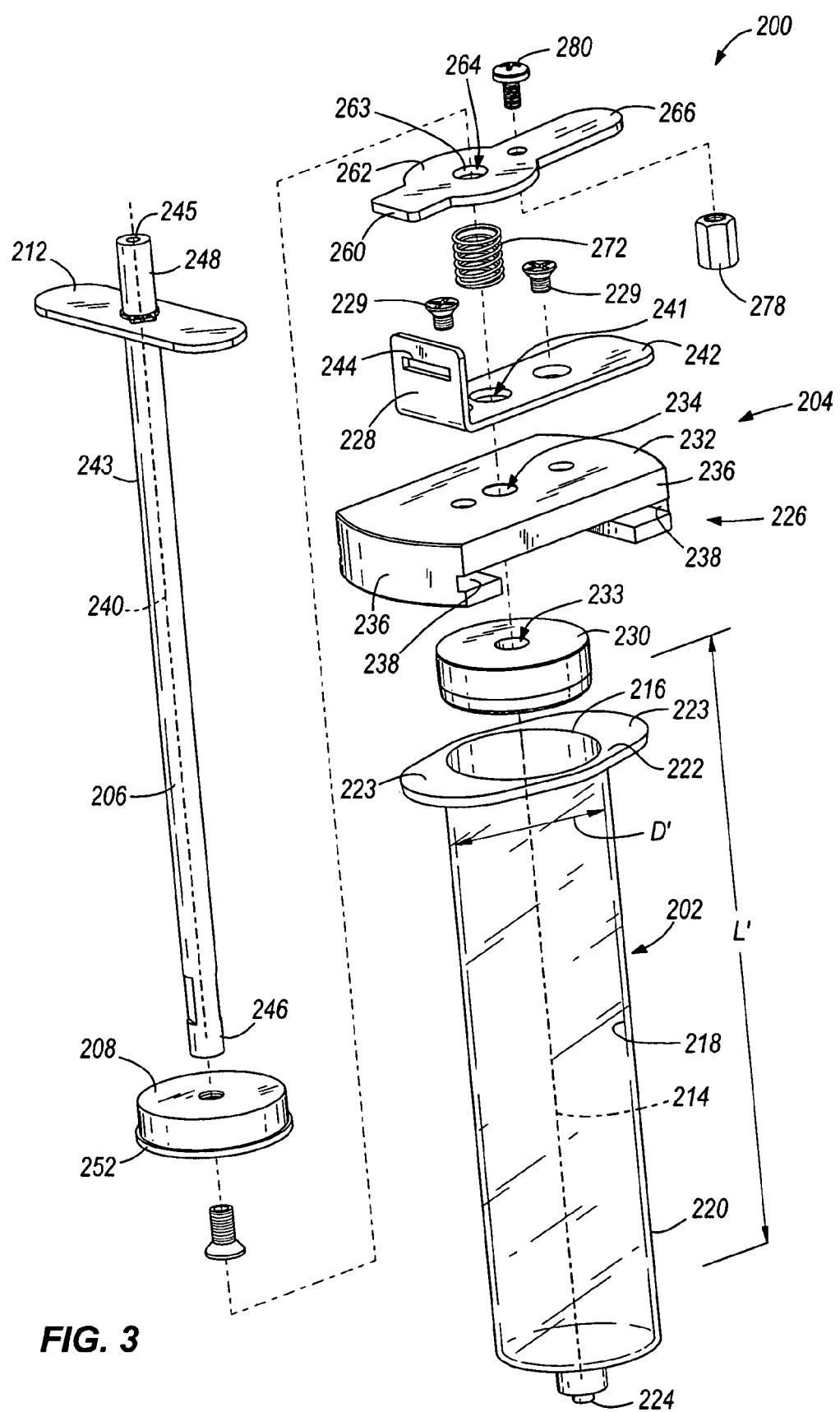
FIG. 3 is an exploded view of a sample injection apparatus according to another embodiment of the present invention.

FIG. 3 illustrates a sample injection apparatus 200 according to another embodiment of the present invention, wherein like numerals represent like elements. The sample injection apparatus 200 shares many of the same elements and features described above with reference to the illustrated embodiment of FIGS. 1-2. Accordingly, elements and features corresponding to elements and features in the illustrated embodiment of FIGS. 1-2 are provided with the same reference numerals in the 200 series. Reference is made to the description above accompanying FIGS. 1-2 for a more complete description of the features and elements (and alternatives to such features and elements) of the embodiment illustrated in FIG. 3.

As shown in FIG. 3, the sample injection apparatus 200 includes a tubular housing 202 that is not pre-filled and does not include a stationary phase, a cap 204, a rod 206, a piston 208, a lever 210, and a handle 212. The tubular housing 202 has a longitudinal axis 214, an open end 216, an inner surface 218, and outer surface 220, a flange 222, an outlet port 224, an inner diameter D', and a length L'.

The cap 204 includes a main portion 226 and a tab 228. The main portion 226 has the same or similar structural features as the main portion 126 described above with reference to FIGS. 1-2, but the main portion 226 is machined out of metal (e.g., anodized aluminum). The cap 204 includes an L-shaped bracket 242 that defines the tab 228. In the embodiment illustrated in FIG. 3, the L-shaped bracket 242 is coupled to the main portion 226 by two screws 229. However, the L-shaped bracket 242 can be coupled to the main portion 226 in any of the variety of manners described above with respect to the L-shaped bracket 142.

With continued reference to FIG. 3, an outer surface or edge 252 of the piston 208 contacts the inner surface 218 of the tubular housing 202 when the piston 208 is positioned within the tubular housing 202. The piston 208 is formed of PTFE (e.g., TEFLON®-brand PTFE). PTFE is less rigid and more deformable than the metal piston 108 illustrated in FIGS. 1 and 2. Depending on the material make-up of the tubular housing 202, the piston 208 may deform when positioned within the tubular housing 202, the piston 208 may at least partially deform the tubular housing 202, or the piston 208 and the tubular housing 202 may both at least partially deform to create a fluid seal. Accordingly, the tubular housing 202 can be formed of a variety of materials including glass, stainless steel, ceramic, polyethylene, polypropylene, polyethylene terephthalate (PET), polyamide, polyvinyl chloride, polytetrafluoroethylene (e.g., Teflon®-brand polytetrafluoroethylene (PTFE), DuPont Corporation), a polymer of tetrafluoroethylene and hexafluoropropylene (FEP; e.g., Dyneon™-brand FEP fluorothermoplastic, 3M Corporation), a fiberglass and PTFE composite (e.g., TEFLEX®-brand fiberglass sheets coated with TEFLON®-brand PTFE, DuPont Corporation), other chemically-inert materials, and the like.

The piston 208 is coupled to a first end 246 of the rod 206 by a hollow screw 231 to maintain fluid communication between a bore 245 in the rod 206 and the tubular housing 202. However, the piston 208 can be coupled to the rod 206 in a variety of suitable manners, including those described above with respect to the piston 108 illustrated in FIGS. 1 and 2.

The following method can be used to prepare the sample of interest for injection into a chromatography system, using the sample injection apparatus 200. First, the sample of interest is dissolved in a first solvent in a container separate from the tubular housing 202. A first stationary phase can then be added to the sample and first solvent to allow the sample to adsorb to the first stationary phase. The first solvent can be removed from the first stationary phase using at least one of heat, vacuum pressure, evaporation (e.g., with a rotary evaporator (Rotovap)), gravity, time, and combinations thereof. The first stationary phase then includes the sample of interest and is at least partially coated with the sample of interest. A first frit (similar to the first frit 113 shown in FIGS. 1 and 2) can be positioned within the tubular housing 202, and the at least partially coated first stationary phase can then be loaded into the tubular housing 202 above the first frit. The first stationary phase can be loaded into the tubular housing 202 using at least one of decanting, scooping, and the like. A second frit (similar to the second frit 115 shown in FIGS. 1 and 2) can then be positioned in the tubular housing 202 above the first stationary phase. The second frit can be packed downwardly to tightly pack the first stationary phase in the tubular housing 202 between the first and second frits. The sample can then be injected into a chromatography system using the method described below.

Whether the sample injection apparatus 100 illustrated in FIGS. 1 and 2, or the sample injection apparatus 200 illustrated in FIG. 3 is used, the following method can be used to inject the sample of interest into a chromatography system after the first stationary phase 101 within the tubular housing 102, 202 has been at least partially coated with the sample of interest using one of the methods described above. The rod 106, 206 can be pressed downwardly in the second direction 176 to move the piston 108, 208 in the second direction 176 within the tubular housing 102, 202 until it contacts the second frit 115. This can be performed manually or with other equipment. The outer edge 152, 252 of the piston 108, 208 can create a fluid seal with the inner surface 118, 218 of the tubular housing 102, 202 to substantially prevent the sample and any solvent from leaking above the piston 108, 208. The sample injection apparatus 100, 200 can then be positioned in fluid communication with a fluid line of a chromatography system. The second solvent used in the chromatography process can then be flown through the bore 145, 245 of the rod 106, 206 out the center of the piston 108, 208, into the at least partially coated first stationary phase 101 to remove the sample of interest from the first stationary phase 101, out the outlet port 124, 224 of the tubular housing 102, 202, and into a chromatography system (e.g., an inlet of a chromatography cartridge).

During sample injection, the lever 110, 210 is biased by the spring 172, 272 in the first position 168 (see FIG. 1) such that the inner surface 163, 263 of the lever 110, 210 is in contact with the outer surface 143, 243 of the rod 106, 206. As shown in FIG. 1, the lever 110, 210 can be positioned at an acute angle with respect to the longitudinal axis 140, 240 of the rod 106, 206. When the lever 110, 210 is positioned in the first position 168, the rod 106, 206 is substantially prevented from movement in the first direction 174, but movement in the second direction 176 is allowed, so that the piston 108, 208 can be pressed downwardly relative to the tubular housing 102, 202 without backing out of the tubular housing 102, 202. When movement in the first direction 174 is desired (e.g., after injection of the sample into the chromatography system, or during injection of the sample), the lever 110, 210 can be pressed downwardly toward the cap 104, 204, against the bias of the spring 172, 272. The boss 178, 278 is positioned to contact the cap 104, 204 to define a second position 170 (see FIG. 1) of the lever 110, 210. When the lever 110, 210 is in the second position 170, the lever 110 is positioned at a substantially right angle with respect to the longitudinal axis 140, 240 of the rod 106, 206. Accordingly, the inner surface 163, 263 of the lever 110, 210 is not contacting (or is minimally contacting) the outer surface 143, 243 of the rod 106, 206, and movement of the rod 106, 206 is allowed in both the first direction 174 and the second direction 176.

Various features and aspects of the invention are set forth in the following claims.

What is claimed is:

1. An apparatus for injecting a sample into a chromatography system, the apparatus comprising:
    a tubular housing having a longitudinal axis, an open end, an inner surface and an outwardly-protruding flange adjacent the open end;
    a cap dimensioned to cover the open end of the tubular housing, the cap including
        a plug portion dimensioned to be received within the open end of the tubular housing, and
        a gripping portion coupled to at least a portion of the flange of the tubular housing;
    a rod having a longitudinal axis generally parallel with the longitudinal axis of the tubular housing, the rod having a first end and a second end;
    a piston coupled to the first end of the rod, the piston protruding outwardly from the rod to define an outer surface, the outer surface dimensioned to engage the inner surface of the tubular housing when positioned within the tubular housing;
    a lever pivotally coupled to the cap and movable between a first position in which the lever engages the rod to substantially prevent movement of the rod in a first direction while allowing movement in a second direction substantially opposite the first direction and a second position in which the lever allows movement of the rod in the first direction and the second direction; and
    a biasing element positioned to bias the lever in the first position.

2. The apparatus of claim 1, wherein the cap includes an aperture and the lever includes an aperture, and wherein the rod is positioned through both the aperture in the cap and the aperture in the lever.

3. The apparatus of claim 2, wherein the biasing element is positioned around the rod between the lever and the cap.

4. The apparatus of claim 2, wherein the aperture in the lever is dimensioned such that the lever is in the first position when the lever is positioned at an acute angle with respect to the longitudinal axis of the rod and the lever is in the second position when the lever is positioned at a substantially right angle with respect to the longitudinal axis of the rod.

5. The apparatus of claim 1, wherein the plug portion and the gripping portion of the cap form a main portion of the cap, and wherein the cap further includes a tab extending outwardly from the main portion, the tab including a slot dimensioned to receive at least a portion of the lever to allow the lever to pivot about the slot to move between the first position and the second position.

6. The apparatus of claim 1, wherein the lever includes a boss positioned to contact the cap to define the second position of the lever.

7. The apparatus of claim 1, wherein the tubular housing is generally cylindrical and has a length, and wherein the tubular housing has a substantially constant cross-section along its length.

8. The apparatus of claim 1, wherein the lever is positioned at an acute angle with respect to the longitudinal axis of the rod when the lever is in the first position.

9. The apparatus of claim 1, wherein the lever wedges against the rod in the first position.

10. The apparatus of claim 1, wherein the outer surface of the piston deforms the tubular housing when the piston is positioned within the tubular housing.

11. The apparatus of claim 1, wherein the lever is positioned outside of the tubular housing.

12. An apparatus for injecting a sample into a chromatography system, the apparatus comprising:
   a tubular housing having a longitudinal axis, an open end, an inner surface and an outwardly-protruding flange adjacent the open end;
   a cap dimensioned to cover the open end of the tubular housing, the cap having an aperture therethrough, the cap including
      a plug portion dimensioned to be received within the open end of the tubular housing, and
      a gripping portion coupled to at least a portion of the flange of the tubular housing;
   a rod having a longitudinal axis generally parallel with the longitudinal axis of the tubular housing, the rod positioned through the aperture in the plug portion of the cap and having a first end and a second end;
   a piston coupled to the first end of the rod, the piston protruding outwardly from the rod to define an outer surface, the outer surface dimensioned to engage the inner surface of the tubular housing when positioned within the tubular housing;
   a lever having an aperture through which the rod is positioned, the lever pivotally coupled to the cap and movable between a first position in which the lever engages the rod to substantially prevent movement of the rod in a first direction while allowing movement in a second direction substantially opposite the first direction and a second position in which the lever allows movement of the rod in the first direction and the second direction, wherein the lever is positioned at an acute angle with respect to the longitudinal axis of the rod when in the first position, and wherein the lever is positioned at a substantially right angle with respect to the longitudinal axis of the rod when in the second position; and
   a biasing element positioned to bias the lever in the first position.

13. The apparatus of claim 12, wherein the outer surface of the piston deforms the tubular housing when in engagement with the inner surface of the tubular housing.

* * * * *